United States Patent [19]

Hall et al.

[11] Patent Number: 4,524,466

[45] Date of Patent: Jun. 25, 1985

[54] CONTINUOUS ROTATION REVERSIBLE PITCH AXIAL THRUST HEART PUMP

[75] Inventors: Charles W. Hall; Orin M. Anderson, both of San Antonio, Tex.

[73] Assignee: Southwest Research Institute, San Antonio, Tex.

[21] Appl. No.: 556,654

[22] Filed: Nov. 30, 1983

[51] Int. Cl.³ .................... A61F 1/00; A61F 1/24; A61M 1/03
[52] U.S. Cl. .................... 603/3; 128/1 D; 417/389; 417/390; 417/413; 417/423 R
[58] Field of Search ......... 3/1.7, 1; 128/1 D, DIG. 3; 417/389, 390, 394, 395, 423 R, 413, 418

[56] References Cited

U.S. PATENT DOCUMENTS

| | | | |
|---|---|---|---|
| 3,568,214 | 3/1971 | Goldschmied | 3/1.7 |
| 3,606,592 | 9/1971 | Madurski et al. | 3/1.7 |
| 3,874,002 | 4/1975 | Kurpanek | 3/1.7 |
| 4,173,796 | 11/1979 | Jarvik | 3/1.7 |
| 4,468,177 | 8/1984 | Strimling | 128/1 D X |

FOREIGN PATENT DOCUMENTS 634752 12/1978 U.S.S.R. .................... 3/1.7

*Primary Examiner*—Ronald L. Frinks
*Attorney, Agent, or Firm*—Fulbright & Jaworski

[57] ABSTRACT

A continuous and unidirectional rotation reversible pitch axial thrust heart pump having a blood handling housing with first inlet and outlet check valves connected to the housing and second inlet and outlet check valves connected to the housing. A first diaphragm is movable in the housing for alternately pumping blood into the first inlet and out of the first outlet valve. A second diaphragm is movable in the housing for alternately pumping fluid into second inlet and out of the second outlet valve. A continuous and unidirectional rotating axial thrust pump is positioned in a hydraulic fluid chamber between the diaphragms. The impeller includes a plurality of blades rotatably mounted on a circular bearing which is rotatably mounted in the housing. The pitch angle of the blades is alternately rotated and reversed which alternately directs the hydraulic fluid to each of the diaphragms that alternately pumps fluid into and out of the housing. The reversing means may include first and second circular drive rotors connected on opposite sides of the impeller blades and alternately actuated. In addition, first and second electrical brushless motors may be provided to drive the first and second rotors, respectively. Each of the rotors includes rotatable means engaging each of the blades for rotating the blades and changing their pitch angle when one of the rotors is moved relative to the other.

8 Claims, 5 Drawing Figures

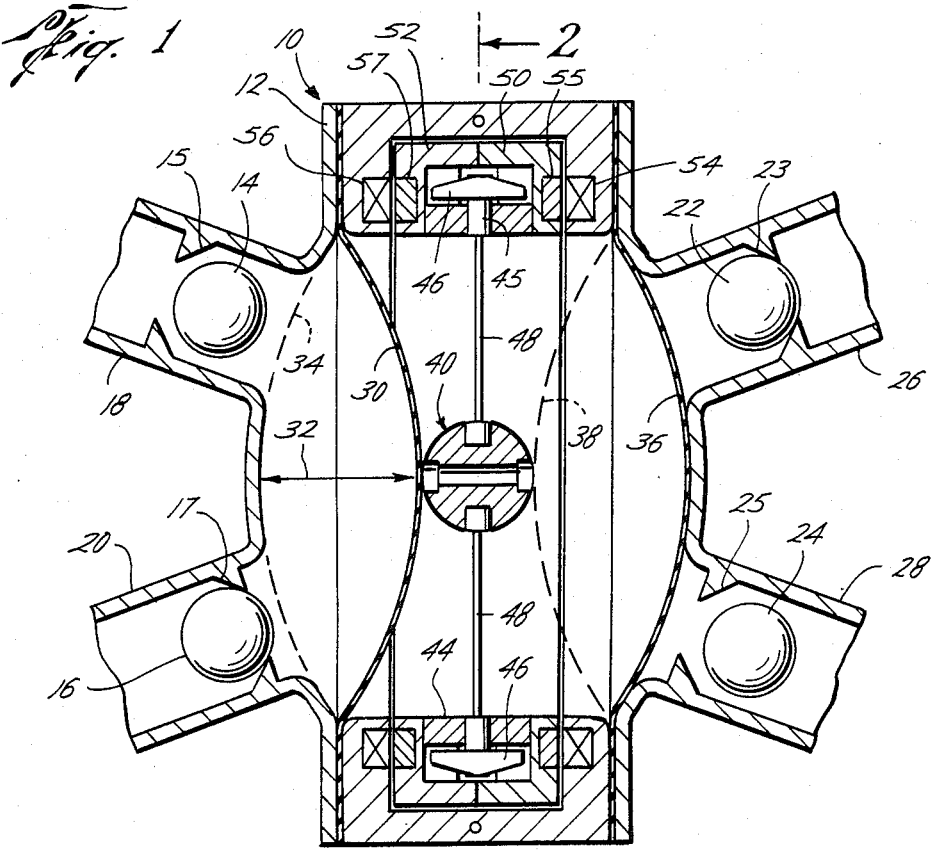
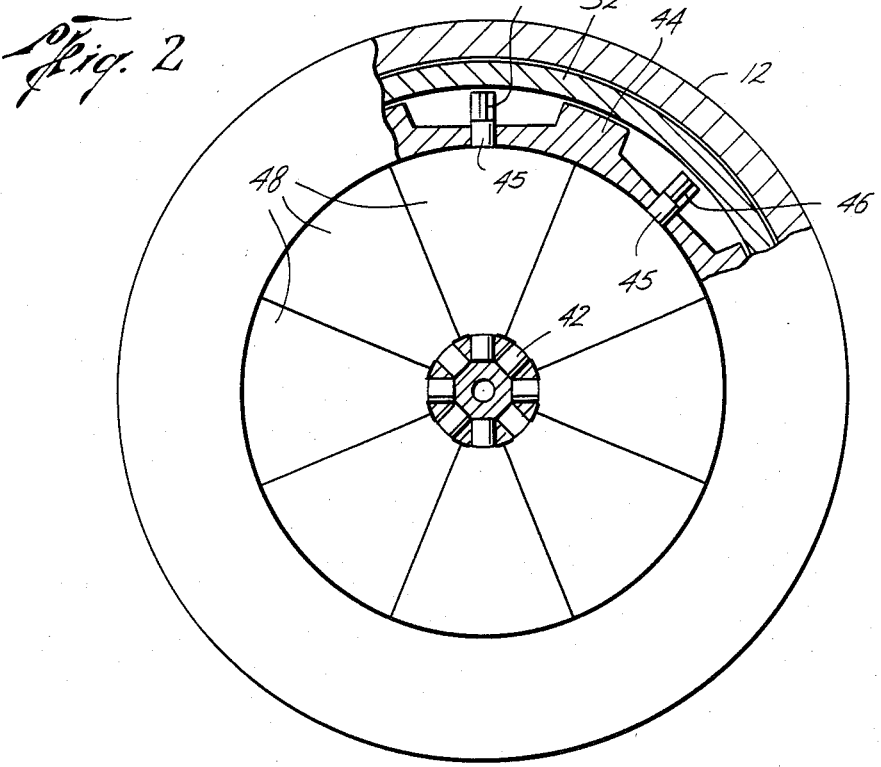

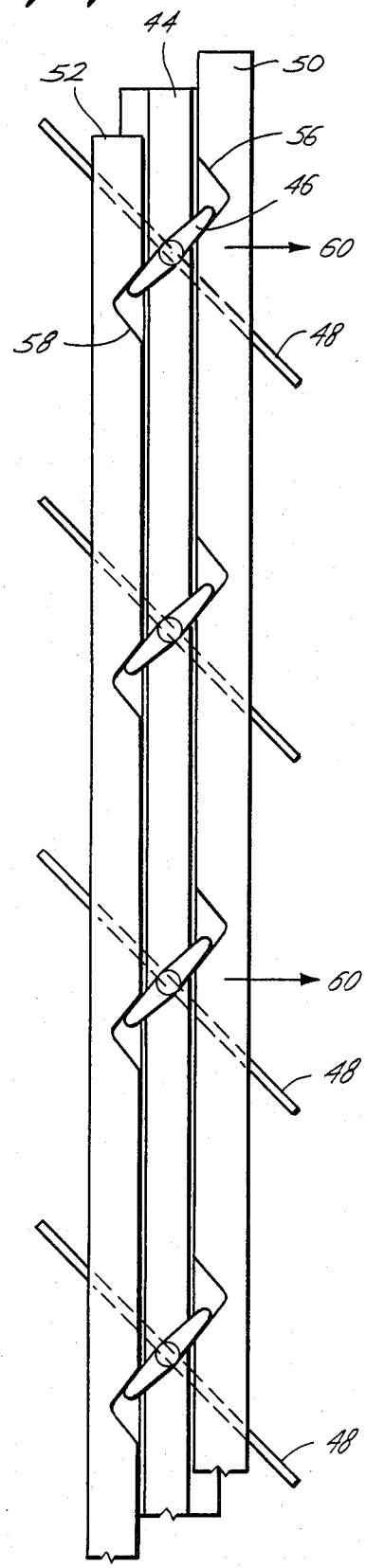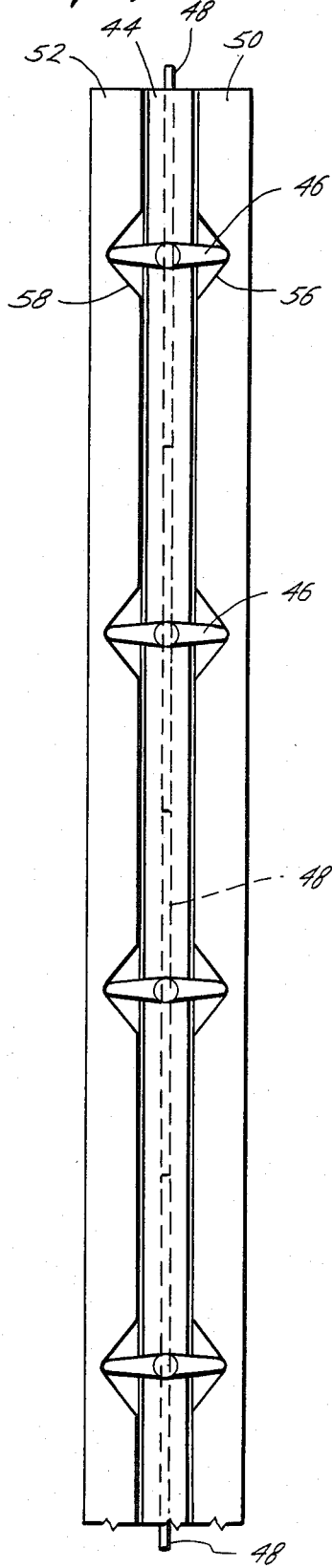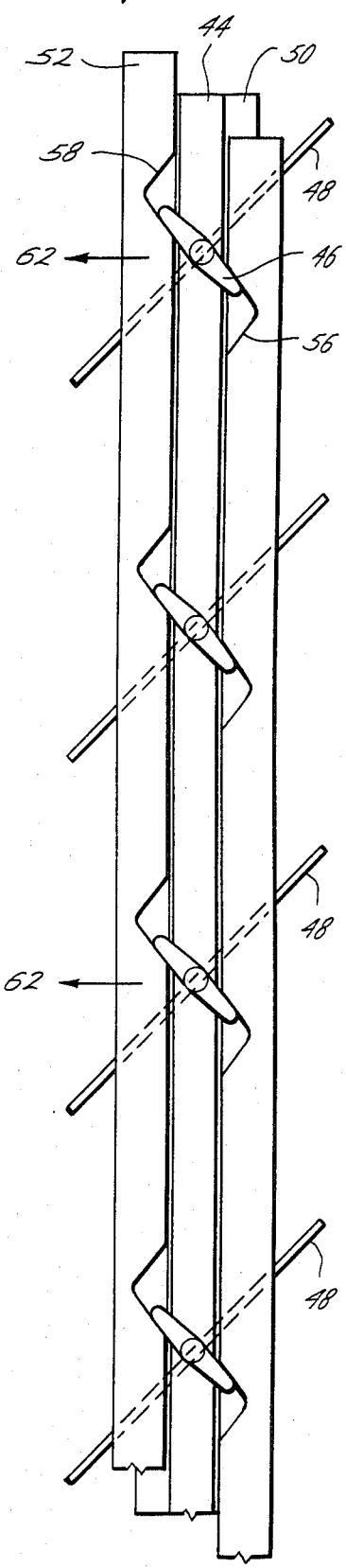

CONTINUOUS ROTATION REVERSIBLE PITCH AXIAL THRUST HEART PUMP

BACKGROUND OF THE INVENTION

One purpose for developing a permanently implanted total artificial heart would be to replace a diseased, failing heart that would in the immediate future cause the patient's demise. Another use for an artificial heart is as a temporary blood pump to keep a patient alive while awaiting a suitable donor transplant heart. Another use would be to use it externally as equipment to pump blood during open heart surgery or during hemodialysis.

Gas energized artificial hearts have been used and do well as temporary blood pumps to fill the hiatus between total failure of the natural heart and a suitable allograph transplant. However, gas energized systems are unsuitable for permanent replacement because the gas cannot be contained in the closed system for prolonged periods of time. Turbine powered hydraulic pumps that have been used for pumping blood are of two types. The Jarvik pump uses a reversible brushless motor that goes from about 10,000 rpm in one direction to 10,000 rpm in the opposite direction in a period of 25 milliseconds which in some instances have caused bearing failures. The other type is the "Turbo-Pulsatile Total Replacement Artificial Heart" which uses a turbine that rotates in only one direction but has a valving system that shunts the hydraulic fluid between the right and left pumping chambers. This system is more difficult to install and takes up more space than the natural heart. It would be more desirable to replace the natural heart with an artificial heart in an orthotopic position.

The present invention is directed towards an axial thrust powered hydraulic pump in which the pitch angle of the impeller blades changes to cause the hydraulic fluid to flow in a reverse direction without changing the direction of the blades. That is, the blades rotate continuously and always rotate in the same direction, but the pitch angle of the blades is alternately reversed to provide the pulsed pumping cycle.

SUMMARY

The present invention is directed towards a continuous and unidirectional rotating reversible pitch axial thrust pump artificial heart. The pump includes a housing with a first inlet and outlet valve connected to the housing and a second inlet and outlet valve connected to the housing. A first diaphragm is movable in the housing for alternately pumping fluid from the first inlet and out the first outlet valved blood chamber. A second diaphragm is movable in the housing for alternately pumping fluid from the second inlet and out the second outlet valved blood chamber. A continuous rotating impeller is positioned in the housing between the first and second diaphragms. The impeller includes a plurality of rotating blades. Means are provided for alternately reversing the pitch angle of the blades for alternately supplying a pressure and suction stroke to each of the diaphragms for alternately pumping fluid into and out of the housing by each of the diaphragms.

A still further object of the present invention is the provision wherein the reversing means includes a first and second drive rotor that actuates the blades which have the ability to change the pitch of the blades alternately.

Still a further object of the present invention is wherein first and second electrical motor means are provided for driving the first and second rotors respectively.

Still a further object of the present invention is wherein each rotor includes means for rotating the blades such as gear means or slot means engaging each of the blades for rotating the blades and changing their pitch angle when one of the rotors is moved relative to the other rotor.

Yet a still further object is the provision of a pump having a housing with a first inlet and first outlet check valve connected to the housing and a second inlet and second outlet check valve connected to the housing. A first movable diaphragm alternately pumps blood from the first inlet valve and out of the first outlet valve and a second movable diaphragm alternately pumps fluid from the second inlet valve and out of the second outlet valve. A continuous rotation axial thrust pump is positioned in the housing in a hydraulic fluid between the diaphragms. The impeller includes a plurality of blades rotatably mounted on a circular bearing that is rotatably mounted in the housing. The pitch angle of the blades is alternately reversed for alternately directing the hydraulic fluid to each of the diaphragms for alternately pumping fluid to provide a pulsing effect into and out of the housing by each of the diaphragms.

Other and further objects, features and advantages will be apparent from the following description of a presently preferred embodiment of the invention, given for the purpose of disclosure, and taken in conjunction with the accompanying drawings.

BRIEF DESCRIPTION OF THE DRAWINGS

FIG. 1 is an elevational view, in cross section, of the apparatus of the present invention positioned in the middle of a cycle, FIG. 2 is a cross-sectional view taken along the line 2—2 of FIG. 1, FIG. 3 is a plane development of the inner surfaces of the left and right drive rotors and impeller frame showing the blade pitch with a right rotor drive, FIG. 4 is a view similar to FIG. 3 with the exception that both rotors are in neutral, and FIG. 5 is a view similar to FIG. 3 showing the vane pitch of the blades with a left rotor drive.

DESCRIPTION OF THE PREFERRED EMBODIMENT

While the present invention is particularly useful and suitable to be used as an implantable artificial heart, it is also useful as a heart assist device and/or in conjunction with a blood oxygenator. It would also find use as a blood pump in conjunction with an artificial kidney.

Referring now to the drawings, particularly to FIG. 1, the reference numeral 10 generally indicates the pump of the present invention and generally includes a housing 12 preferably contoured for replacing a natural heart in an orthotopic position. A first inlet check valve 14 and a first outlet check valve 16 are connected to the housing 12. When suction is applied in the housing 12 against the valves 14 and 16 the outlet check valve 16 seats on a valve seat 17, but the check valve 14 moves off of a seat 15 allowing fluid from inlet line 18 to pass through the check valve 14 and into the housing 12. On the other hand, when pressure is exerted in the housing 12 against the valves 14 and 16, the inlet check valve 14 seats on its seat 15 and fluid in the housing 12 adjacent the check valve 16 will move the check valve 16 off of its seat 17 and expel the fluid through the line 20. Similarly, a second inlet check valve 22 and a second outlet check valve 24 are connected to the housing 12.

A first diaphragm 30 is movable in the housing 12 and covers the inlet line 18 and the outlet line 20 and the check valves 14 and 16. Movement of the diaphragm 30 to and from the valves 14 and 16 will alternately pump fluid between the diaphragm 30 and the valves 14 and 16 out of the outlet valve 16 and in through the inlet valve 14. The stroke of the diaphragm 30, as indicated by the line 32 and as shown in FIG. 1 in full outline, is at the end of the suction stroke. When the diaphragm 30 is at the position indicated in dotted outline 34, it is at the end of its pressure stroke.

Similarly, a second diaphragm 36 is provided in the housing 12 enclosing the inlet check valve 22 and the outlet check valve 24. When the diaphragm 36 is at the end of its pressure stroke, as indicated in the solid outline 36, the suction check valve 22 is seated on its valve seat 23 in the line 26 while the outlet check valve 24 is off of its seat 25 in the line 28 whereby fluid is being expelled from the housing 12 through the line 28. When the diaphragm 36 is at the extent of its suction stroke it is in position 38, as indicated in dotted outline, the inlet valve 22 would be opened bringing in fluid through the line 26 and the outlet check valve 24 would be closed.

Referring now to FIGS. 1 and 2, a continuous rotation axial thrust pump impeller generally indicated by the reference numeral 40 is positioned in the housing between the first and second diaphragms 30 and 36 in a hydraulic fluid. The pump 40 generally includes a hub 42, a circular bearing 44 which is rotatable in the housing 12. The pump impeller 40 includes a plurality of blades 48 which are rotatably connected to each of the hub 42 and bearing 44. The blades 48 are connected to bearing 44 by pivoting shafts 45, each of which are connected to a control dog 46. The control dogs 46 are in a plane perpendicular to the blades 48.

Means are provided for alternately rotating and reversing the pitch angle of the blades 48 for alternately directing the hydraulic fluid between the diaphragms 30 and 38 to each of the diaphragms for alternately pumping fluid into and out of the housing by each of the diaphragms. Preferably, a first circular drive rotor 50 and a second left drive rotor 52 are provided connected on opposite sides of the dogs 46 for rotating and reversing the angle of the blades 48 as the rotors 50 and 52 are alternately actuated. The rotors 50 and 52 are driven by any suitable first and second electrical motor means such as brushless rotors which include fixed fields 54 and 56 and rotor drives 55 and 57, respectively, which are connected to and which drive the rotors 50 and 52, respectively.

Referring now to FIGS. 3, 4 and 5, the plane development of the rotors 50 and 52 and the dogs 46 and thus of the connected blades 48 is best seen. Referring now to FIG. 3, it is noted that each of the rotors 50 and 52 include blade axial rotating means such as suitable gear means or slots 56 and 58, respectively, that are engageable with the dogs 46. The rotors 50 and 52 are always rotated in the same direction, such as in the clockwise direction as viewed in FIG. 2. In FIG. 3, the rotor 50 is being driven ahead of the rotor 52. This causes the rotor 50 to move forwardly relative to the rotor 52 and the slots 56 and 58 coact with the dogs 46 to rotate the blades 48 so that the pitch causes hydraulic fluid to be driven to the right as indicated by the arrows 60. The pitch in this case would cause a suction on the left diaphragm 30 and a positive pressure pulse to be exerted on the right-hand diaphragm 36.

Referring now to FIG. 5, the right-hand rotor 52 has been driven ahead of the right-handed rotor 52. However, the blades rotate in the same direction continuously. However, movement of the left rotor 52 ahead of the right rotor 50 allows the slots 56 and 58, respectively, to rotate the dogs 46 and thus the blades 48 and change their pitch whereby the hydraulic fluid between the diaphragms 30 and 36 is being pulsed to the left as indicated by the arrows 62. In this event, the diaphragm 60 is subject to a positive pulse thereby expelling fluid out the first check valve 16 while the diaphragm 36 is subjected to a suction pulse thereby drawing blood through the second inlet check valve 22.

FIG. 4 indicates the neutral position of the rotors 50 and 52 relative to each other such as the initial position when neither of the rotors 50 and 52 are being driven, and also indicates an intermediate position (FIG. 1) between the left side drive of FIG. 3 and the right side drive of FIG. 5.

While any suitable control means may be used to drive the rotors 50 and 52, it is preferred to change the pitch of the blades 48 by slowing down or speeding up one of the motors by altering the power to the motors to move one of the rotors relative to the other and drive both rotors at the same speed.

For an artificial heart application, the use of the brushless motors rather than a shaft driven system would appear beneficial. Also, for an artificial heart application, the impeller pump 10 may be sized and located between the two ventricles so that the pump 10 could be placed in an orthotopic position.

The hydraulic system is separated from the blood pumping chambers by the flexible diaphragms 30 and 36. Each ventricle would, therefore, be alternately pulsed rather than simulating the biological synchronization. The blood pumping chambers (ventricles) would have an inflow and an outflow valve to maintain unidirectional blood flow. The various components of the pump are made of suitable materials for its application as suggested by those skilled in the art.

The present invention, therefore, is well adapted to carry out the objects and attain the ends and advantages mentioned as well as others inherent therein. While a presently preferred embodiment of the invention has been given for the purpose of disclosure, numerous changes in the details of construction and arrangement of parts will be readily apparent to those skilled in the art and which are encompassed within the spirit of the invention and the scope of the appended claims.

What is claimed is:

1. A continuous rotation reversible pitch impeller heart pump comprising,
   a housing,
   a first inlet and outlet valve connected to the housing,
   a second inlet and outlet valve connected to the housing,
   a first diaphragm movable in the housing for alternately pumping fluid from the first inlet and out of the first outlet valve,
   a second diaphragm movable in the housing for alternately pumping fluid from the second inlet and out of the second outlet valve,
   a continuous rotation impeller thrust pump positioned in the housing between the first and second diaphragms, said impeller including a plurality of rotating blades, and means for alternately reversing the pitch angle of said blades for alternately applying a pressure and suction stroke to each of the diaphragms for alternately pumping fluid into and out of the housing by each of the diaphragms.

2. The apparatus of claim 1 wherein the reversing means includes, first and second drive rotors connected by slot means to the blades for rotating the blades axially for changing the pitch angle.

3. The apparatus of claim 2 including, first and second electrical motor means for driving the first and second rotors, respectively.

4. The apparatus of claim 2 wherein each rotor includes gear means engaging each of the blades for rotating the blades and changing their pitch angle when one of the rotors is moved relative to the other rotor.

5. A continuous rotation reversible pitch impeller heart pump comprising, a housing, a first inlet and outlet check valve connected to the housing, a second inlet and outlet check valve connected to the housing, a first diaphragm movable in the housing for alternately pumping blood from the first inlet and out of the first outlet valve, a second diaphragm movable in the housing for alternately pumping fluid from the second inlet and out of the second outlet valve, hydraulic fluid positioned in the housing between the diaphragms, a continuous rotation unidirectional impeller pump positioned in the housing between the diaphragms, said impeller including a plurality of blades rotatably mounted on a circular bearing which is rotatably mounted in the housing, and means for alternately axially rotating and reversing the pitch angle of said blades for alternately directing the hydraulic fluid to each of the diaphragms for alternately pumping blood into and out of the housing by each of the diaphragms.

6. The apparatus of claim 5 wherein the reversing means includes, first and second circular drive rotors connected on opposite sides of the impeller and movable relative to the blades and each other.

7. The apparatus of claim 6 including, first and second electrical motor means for driving the first and second rotors, respectively.

8. The apparatus of 7 wherein each rotor includes slot means engaging each of the blades for axially rotating the blades and changing their pitch angle.

* * * * *